United States Patent [19]

Reddy et al.

[11] Patent Number: 5,156,957
[45] Date of Patent: * Oct. 20, 1992

[54] FOLLICLE STIMULATING HORMONE

[75] Inventors: Vemuri B. Reddy, Framingham; Nancy Hsiung, Wellesley; Anton K. Beck, Chesnut Hill; Edward G. Berstine, Boston, all of Mass.

[73] Assignee: Genzyme Corporation, Boston, Mass.

[*] Notice: The portion of the term of this patent subsequent to May 8, 2007 has been disclaimed.

[21] Appl. No.: 323,665

[22] Filed: Apr. 24, 1989

Related U.S. Application Data

[63] Continuation of Ser. No. 696,647, Jan. 30, 1985, Pat. No. 4,923,805, which is a continuation-in-part of Ser. No. 548,228, Nov. 2, 1983, Pat. No. 4,840,896.

[51] Int. Cl.$^5$ .................. C12P 21/06; C12P 21/02; C12N 5/00; C07K 3/00
[52] U.S. Cl. ..................... 435/69.4; 435/240.2; 435/320.1; 435/172.3; 435/70.1; 530/395
[58] Field of Search ................. 435/69.1, 69.4, 172.3, 435/210.2, 320, 13, 66, 70

[56] References Cited

U.S. PATENT DOCUMENTS

| | | | |
|---|---|---|---|
| 4,840,896 | 6/1989 | Reddy et al. | 435/68 |
| 4,923,805 | 5/1990 | Reddy et al. | 435/69.4 |

OTHER PUBLICATIONS

Pierce et al., (1981) Ann. Rev. Biochem vol. 50, pp. 465–496.
Fiddes et al. (1980) Nature vol. 286, pp. 684–687.
Chappel, Scott et al. (1983) Endocrine Reviews vol. 4 #2 pp. 179–211.
Fiddes et al. (1981) J. Mol. Appl. Gene. vol 1, pp. 3–18.
Elder, J. T. et al. Ann Rev. Genet. vol 15, pp. 328–330, (1981).
Rice, D. et al. (1982) Proc. Natl. Acad. Sci. vol. 79 pp. 7862–7865.
Moriarty, A. et al. (1981) Proc. Natl. Acad. Sci. vol. 78, pp. 2606–2610.
Lusthader, J. et al. (1986) 68th Annual Meeting of the Endocrine Society, Abstract #513.
Chemical Abstracts, vol. 108, No. 3 issued 1987, 18 Jan. (Columbus, Ohio, USA), Stewart, F. "Application of Recombinant DNA Techniques to Structure-Function Studies of Equine Protein Hormones" See p. 147, col. 1–2, Abstract No. 17058w, J. Reprod. Fertil. Suppl. (1987) 35: 1–8.
Chemical Abstracts, vol. 107, No. 17 issued 1987, 26 Oct. (Columbus, Ohio, USA), Nilson, J. "Expression of the Genes Encoding Bovine LH in a Line of Chinese Hamster Ovary Cells" See p. 187, col. 2, Abstract No. 148529C, J Reprod. Fertil. Suppl. (1987) 34: 227–36.
Chemical Abstracts, vol. 106, No. 17, issued 1987, 27 Apr. (Columbus, Ohio, USA) Schwartzbouer, J. "Efficient and Stable Expression of Recombinant Fibronectin Polypeptides" See p. 173, col. 1, Abstract No. 132796f Proc. Natl Acad Sci USA (1987) 84: 754–8.
Chemical Abstracts, vol. 103, No. 7, issued 1985, 19 Aug. (Columbus, Ohio USA) Reddy, V. "Heterodimeric Human Fertility Hormones" See p. 146, col. 1, Abstract No. 49165d, PCT WO 85 01958, 9 May 1985.
Chemical Abstracts, vol. 103, No. 9, issued 1985, 2 Sep. (Columbus, Ohio USA) Reddy, V. "Heterodimeric Human Fertility Hormones", See p. 182, col. 1–2, Abstract No. 66081d, PCT WO 85 01959, 9 May 1985.
Kaetzel, D. et al. (5 May 1988) J. Biol. Chem. vol. 263: 6344–6351 Methotrexate-Induced Amplification of the Bovine Lutropin Genes in Chinese Hamster Ovary Cells. Relative Concentration of the Alpha and Beta Subunits Determines the Extent of Heterodimer Assembly.
Kaetzel, D. et al. (Nov. 1985) Proc. Natl. Acad. Sci. USA, vol. 82: 7820–7283 Expression of Biologically Active Bovine Luteinizing Hormone in Chinese Hamster Ovary Cells.
Chemical Abstracts, vol. 109, No. 7 issued 1988, 14 Aug. (Columbus, Ohio, USA), Kato, Y. "Cloning and DNA Sequence Analysis of the cDNA for the Precursor of Porcine Follicle Stimulating Hormone Beta Subunit" See p. 182, col. 2, Abstract No. 49432a, Mol. Cell. Endocrinol (1988) 55: 107–12.

Primary Examiner—Jacqueline Stone
Assistant Examiner—Gian Wang

[57] ABSTRACT

Biologically active heterodimeric human FSH composed of an alpha subunit and a beta subunit, each subunit being synthesized by a cell having an expression vector containing heterologous DNA encoding the subunit.

10 Claims, 4 Drawing Sheets

FOLLICLE STIMULATING HORMONE

This application is a continuation of application Ser. No. 696,647 filed on Jan. 30, 1985, now U.S. Pat. No. 4,923,805, which in turn is a continuation-in-part of application Ser. No. 548,228 filed Nov. 2, 1983, now U.S. Pat. No. 4,840,896.

BACKGROUND OF THE INVENTION

This invention relates to the use of recombinant DNA techniques to produce heteropolymeric proteins.

Various polypeptide chains have been expressed, via recombinant DNA technology, in host cells such as bacteria, yeast, and cultured mammalian cells. Fiddes, J. C. and Goodman, H. M. (1979) *Nature* Vol. 281, pg. 351–356 and Fiddes, J. C. and Goodman, H. M. (1980) *Nature* Vol. 286, pg. 684–687 describe the cloning of, respectively, the alpha and beta subunits of human choriogonadotropin (hCG).

Sugimoto U.S. Pat. No. 4,383,036 describes a process for producing hCG in which human lymphoblastoid cells are implanted into a laboratory animal, harvested from the animal, and cultured in vitro; accumulated hCG is then harvested from the culture.

SUMMARY OF THE INVENTION

In general the invention features the biologically active heterodimeric human fertility hormone follicle stimulating hormone ("FSH") which includes an alpha subunit and a beta subunit, each subunit being synthesized by a cell having an expression vector containing heterologuous DNA encoding the subunit.

The term "expression vector" refers to a cloning vector which includes heterologous (to the vector) DNA under the control of sequences which permit expression in a host cell. Such vectors include replicating viruses, plasmids, and phages. Preferred vectors are those containing at least the 69% transforming region, and most preferably all, of the bovine papilloma virus genome.

The invention permits the production of biologically active heterodimeric FSH from a single culture of transformed cells. The production of both subunits of FSH in the same cell eliminates the necessity of recombining subunits from separate cultures to assemble an active heterodimeric molecule. The system also allows production of FSH, in a single culture, which undergoes, in the culture, post-translational modification, e.g. glycosylation and proteolytic processing, for activity or stability.

In preferred embodiments, each expression vector is autonomously replicating, i.e., not integrated into the chromosome of the host cell. The use of autonomously replicating expression vectors prevents undesirable influence of the desired coding regions by control sequences in the host chromosome.

Other advantages and features of the invention will be apparent from the following description of the preferred embodiments thereof, and from the claims.

DESCRIPTION OF THE PREFERRED EMBODIMENTS

We turn now to the preferred embodiments of the invention, first briefly describing the drawings thereof.

DRAWINGS

STRUCTURE

Figure 1:
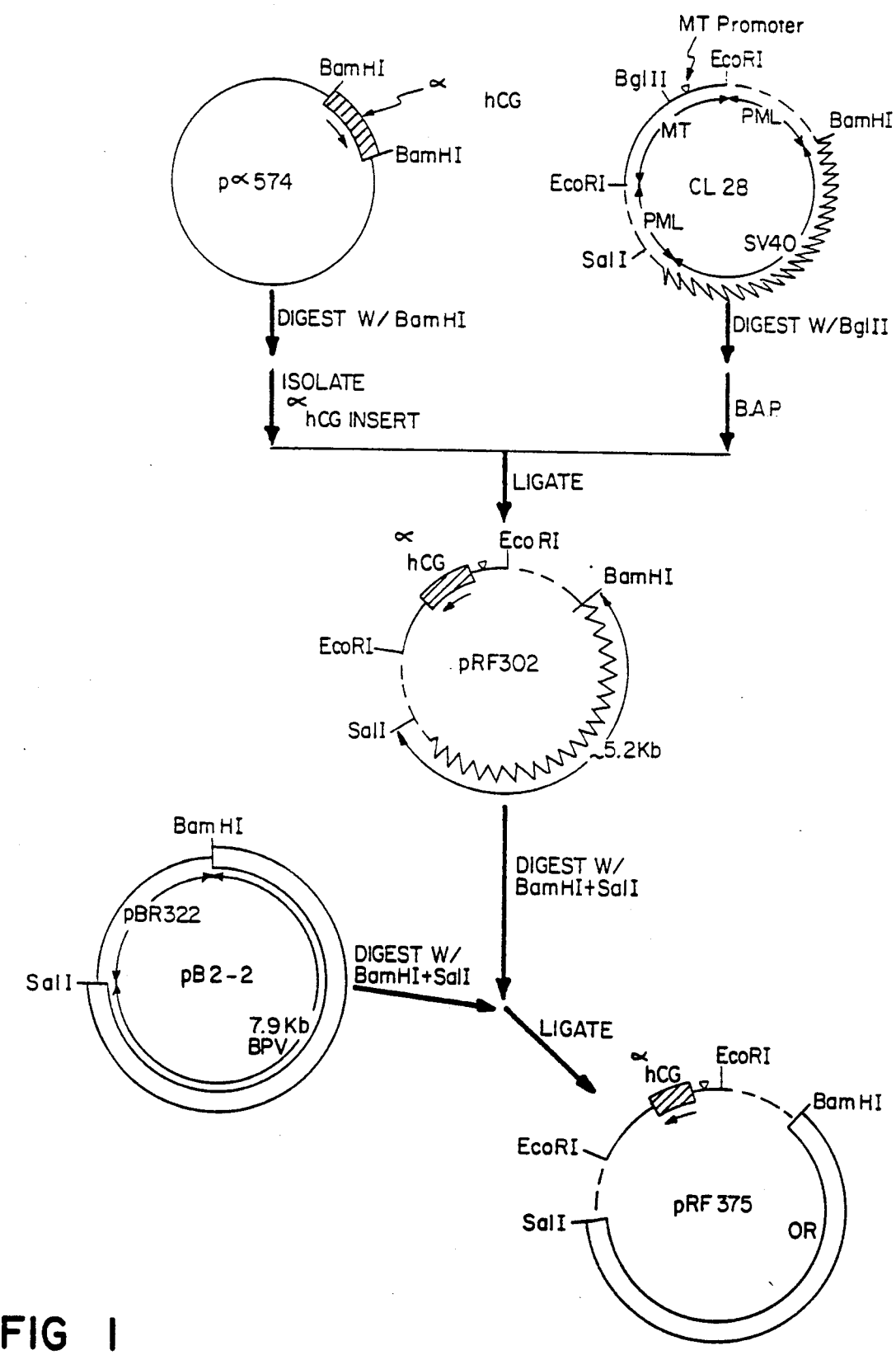
FIG. 1 is a diagrammatic illustration of the construction of the plasmid pRF375.

The cloning vectors of the invention have the general structure recited in the Summary of the Invention, above Preferred vectors have the structures shown in the Figures, and are described in more detail below.

CONSTRUCTION OF CLONING VECTORS

Isolation of cDNA Clones Encoding the Common Alpha Subunit

In order to produce the heterodimeric FSH of the invention, the alpha subunit of human chorionic gonadotropin (hCG) first is isolated; the alpha subunit is common to the fertility hormones hCG, luteinizing hormone (LH), and FSH.

All of the techniques used herein are described in detail in Maniatis et al. (1982) *Molecular Cloning: A Laboratory Manual* (Cold Spring Harbor Laboratory), hereby incorporated by reference.

RNA is extracted from placental tissue by the following method. Homogenization of the tissue is carried out in a 1:1 mixture of phenol:100mM Na-acetate (pH 5.5) containing 1mM EDTA, that has been warmed to 60° C. for 20 min. After cooling on ice for 10 min., the phases are separated by centrifugation. The hot phenol extraction is repeated twice more followed by two extractions with chloroform.

RNA is precipitated from the final aqueous phase by the addition of 2.5 volumes of ethanol.

In order to enrich for poly A+mRNA, placental RNA is passed over oligo (dT)-cellulose in 0.5M NaCl buffered with 10mM Tris-HCl, pH 7.5, and washed with the same solution. Poly A+mRNA is eluted with 10mM Tris-HCl (pH 7.5), 1mM EDTA, 0.05% SDS and precipitated twice with ethanol. Typical initial yields are 1.5–2.0 mg of total RNA per g of tissue, of which about 2% is poly A+mRNA.

Placental cDNA libraries are constructed by reverse transcription of placental mRNA, second strand synthesis using *E. coli* DNA polymerase I (large fragment), treatment with SI nuclease, and homopolymer tailing (dC) with terminal deoxynucleotidyl transferase; all such procedures are by conventional techniques.

In a typical preparation, 20–30% conversion of mRNA to single strand (ss) cDNA; 70% resistance to digestion with nuclease S1 after second strand synthesis; and dC "tails" of ten to twenty-five bases in length, are obtained. These cDNA molecules are then annealed to DNA fragments of the plasmid pBR 322, which has been digested with PstI, and to which dG "tails" have been added. These recombinant plasmids are then used to transform *E. coli* cells to generate a cDNA library (transformed cells are selected on the basis of tetracycline resistance).

In order to identify the human alpha hCG clone, a 219 bp fragment of a mouse alpha thyroid stimulating hormone (TSH) clone is used as a hybridization probe. This probe has 77% sequence homology with the human clone. It is radioactively labeled by nick translation and hybridized to the cDNA library under conditions that take into account the extent of homology. Strongly hybridizing clones are analyzed by restriction mapping and clones containing the complete coding sequence of alpha hCG are verified by DNA sequencing.

Construction of Plasmid pRF375

Referring to FIG. 1, the plasmid CL28 (identical to plasmid JYMMT(E); Hamer et al. (1983) J. Mol. Applied Gen. 1, 273-288), containing the murine metallothionein promoter, SV40 DNA, and pBR322 sequences, is cut with the restriction endonuclease BglII. At this site is inserted the cDNA clone of alpha hCG, containing untranslated regions of about 10 and 220 bp at its 5' and 3' ends, respectively. This clone has been genetically engineered by the addition of synthetic BamHI linkers at its termini.

The resulting plasmid pRF302 is digested with restriction enzymes BamHI and SalI to release the SV40 DNA sequence.

Plasmid pB2-2, which contains the entire BPV genome, and some pBR322 sequences, is digested with BamHI and SalI to yield the BPV genome with BamHI/SalI ends; this fragement is ligated into pRF302 containing the metallothionein-hCG sequences.

Following transformation of E. coli, plasmid pRF375 is identified and isolated. It encodes the common alpha subunit under the control of the mouse metallothionein promoter.

Isolation of the Human beta FSH Gene

A human genomic library in phage lambda (Lawn et al., 1978, Cell 15, p. 1157-1174) is screened using "guessed" long probes. The idea behind such probes, set forth in Jaye et al. (1983) Nucleic Acids Research 11(8), 2325, is that if the amino acid sequence of a desired protein is at least partially known, a long probe can be constructed in which educated guesses are mad as to the triplet encoding any amino acid which can be encoded by more than one, and not more than four, different triplets. Any correct guesses increase the amount of homology, and improve the specificity, of the results.

To isolate desired regions of DNA, two labeled 45-mer probes are used: TB36, homologous with amino acids 56-70 of human beta FSH; and TB21, homologous with amino acids 73-87. These probes have the following nucleotide compositions (corresponding amino acids are also given):

```
TB36:      Val—Tyr—Glu—Thr—Val—Lys—Val—
(AA56-70) 3' CAC ATG CTC TGG CAC TCT CAC

Pro—Gly—Cys—Ala—His—His—Ala—Asp
           GGT CCG ACG CGG GTG GTGCGA CTG 5'

TB21:      Tyr—Thr—Tyr—Pro—Val—Ala—Thr—
(AA73-87) 3' ATG TGC ATG GGT CAC CGA TGT
```

```
           Glu—Cys—His—Cys—Gly—Lys—Cys—Asp
           CTC ACA GTG ACG CCG TTT ACG CTG 5'
```

The above probes are used to screen the human genomic library as follows. TB21 is labeled with $^{32}P$ and used to screen approximately $5 \times 10$, lambda plaques on duplicate filters by the in situ plaque hybridization technique of Benton and Davis (1977) Science 196, 180-182. The prehybridization solution is maintained at 55° C. for several hours and has the following composition: 0.75M NaCl; 0.15M Tris/HCl, pH 8.0; 10mM EDTA; 5 x Denhardt s Solution; 0.1% sodium pyrophosphate; 0.1% SDS; 100 microgram/ml E. coli t-RNA. The hybridization solution has the same composition except that it is maintained overnight at 45° C., and contains labeled probe in a concentration of about $0.5 \times 10^6$ cpm/ml. After hybridization, the filters are washed four times in $1 \times SSC$ (=0.15M NaCl, 0.015M $Na_3$-citrate) and exposed to x ray film.

This screening procedure yields 50 plaques which hybridize to TB21 on both sets of filters. These 50 individual plaques are picked and combined into 10 culture pools containing 5 plaques each. The 10 cultures are grown and DNA is isolated from 50ml phage lysates. This DNA is then digested with EcoRI and fractionated on two identical 1% agarose gels, after which it is transferred to nitrocellulose paper according to the method of Southern (1975) J. Mol. Biol. 98, 503-517.

The DNAs on the two filters are hybridized to $^{32}p$ labeled TB21 and TB36, respectively. Individual plaques from the pool containing a restriction fragment which strongly hybridizes to both probes are then screened according to the above procedure, except that the DNAs are digested with EcoRI, BamHI, and EcoRI plus BamHI. In this way the 6.8kb EcoRI-BamHI fragment containing human beta FSH is isolated.

Figure 2:
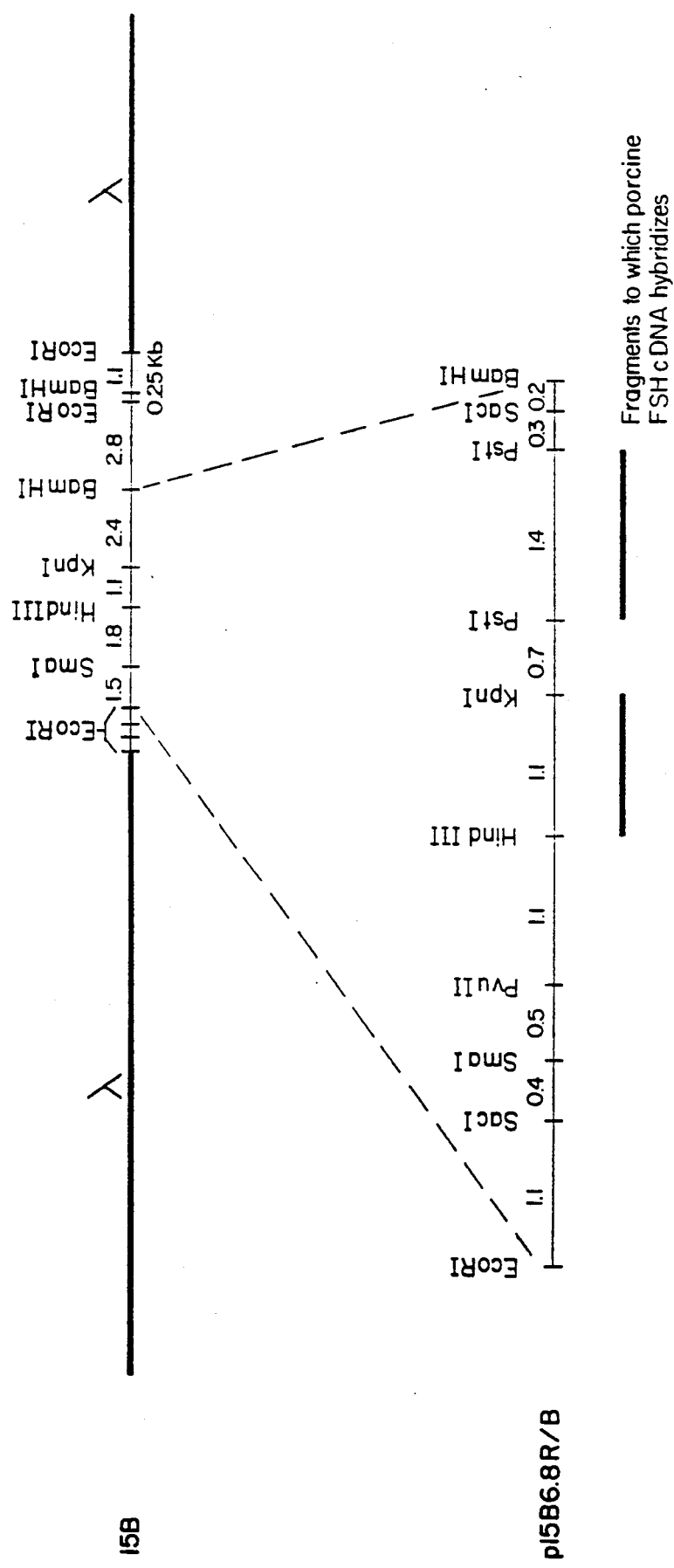
FIG. 2 is a partial restriction map of the lambda clone 15B and the beta FSH-containing 6.8 kb EcoRI-BamHI fragment that is inserted into pBR322.

A partial restriction map of clone 15B, containing the 6.8kb EcoRI-BamHI fragment, is shown in FIG. 2. In order to locate the position of the beta FSH sequences within the clone, the 6.8 kb EcoRI-BamHI fragment of clone 15B is subcloned into pBR322 to yield plasmid p15B6.8R/B (FIG. 2). p15B6.8R/B is then digested with various restriction enzymes and the products are fractionated by agarose gel electrophoresis using conventional methods. The DNA is blotted to nitrocellulose paper and hybridized to fragments of a porcine beta FSH cDNA clone labeled with $^{32}p$ by nick translation.

As shown in FIG. 2, the porcine beta FSH probe hybridizes to only two fragments of the human DNA, namely a 1.1kb HindIII-KpnI and a 1.4kb PstI fragment Partial DNA sequencing of these two fragments shows that this DNA indeed codes for human beta FSH and that the entire coding region for beta FSH is contained in these two fragments.

Figure 3:
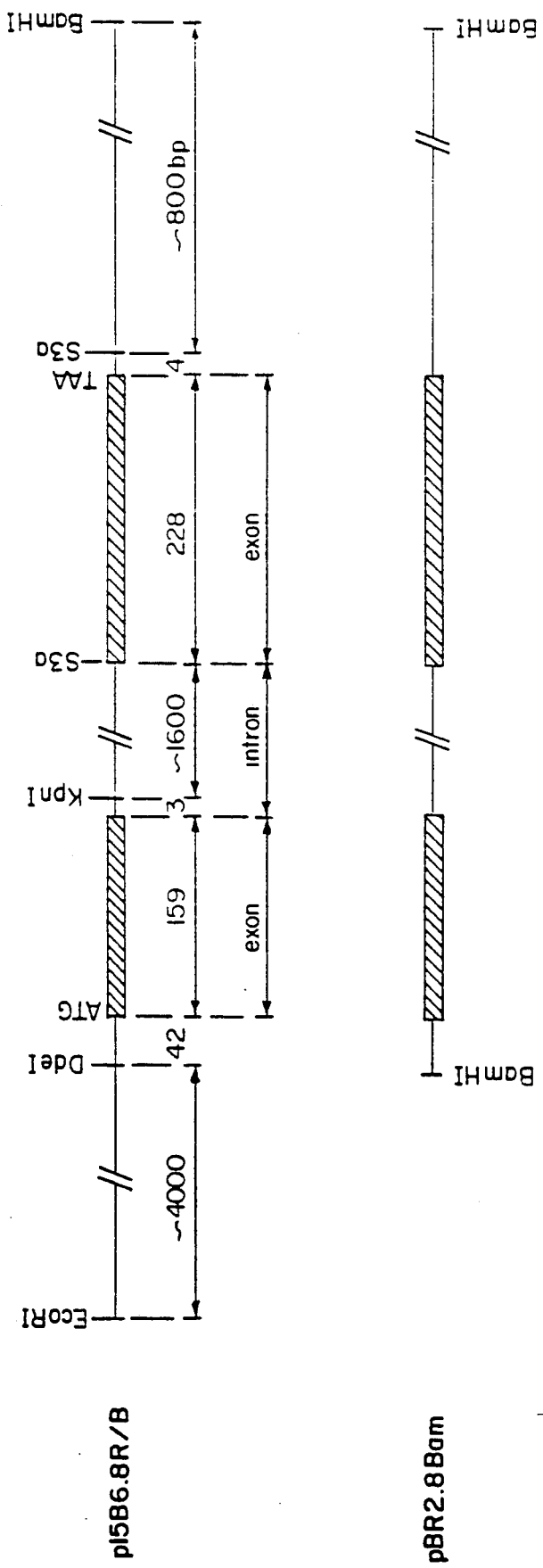
FIG. 3 is a partial restriction map of the beta FSH coding region and the BamHI fragment that is inserted into a BPV based expression vector.

As shown by the restriction map of FIG. 3, the beta FSH coding sequence is interrupted by an intervening sequence of approximately 1.6kb between amino acids 35 and 36 of mature beta FSH. The nucleotide sequence of the entire human beta FSH coding region and some of the flanking and intervening sequences are given below. The amino acid sequence deduced from the nucleotide sequence is given for the coding region.

```
                30                                              60
GCT TAC ATA ATG ATT ATC GTT CTT TGG TTT CTC AGT TTC TAG TGG GCT TCA TTG TTT GCT
```

```
                                    90                                         120
TCC CAG ACC AGG  ATG   AAG ACA CTC CAG TTT TTC TTC CTT TTC TGT TGC TGG AAA GCA ATC
                 Met   Lys Thr Leu Gln Phe Phe Phe Leu Phe Cys Cys Trp Lys Ala Ile 150                                         180
TGC TGC AAT AGC TGT GAG CTG ACC AAC ATC ACC ATT GCA ATA GAG AAA GAA GAA TGT CGT
Cys Cys Asn Ser Cys Glu Leu Thr Asn Ile Thr Ile Ala Ile Glu Lys Glu Glu Cys Arg

210                        ↓        240
TTC TGC ATA AGC ATC AAC ACC ACT TGG TGT GCTGGC TAC TGC TAC ACC AGGTA GGT ACC
Phe Cys Ile Ser Ile Asn Thr Thr Trp Cys Ala Gly Tyr Cys Tyr Thr Arg 270                                  300
/ / ATG TTA GAG CAA GCA GTA TTC AAT TTC TGT CTC ATT TTG ACT AAG CTA AAT AGG AAC

330          ↓                     360
TTC CAC AAT ACC ATA ACC TAA CTC TCT TCT TAA ACT CCT CAG GAT CTG GTG TAT AAG GAC
                                                         Asp Leu Val Tyr Lys Asp 390                                         420
CCA GCC AGG CCC AAA ATC CAG AAA ACA TGT ACC TTC AAG GAA CTG GTA TAT GAA ACA GTG
Pro Ala Arg Pro Lys Ile Gln Lys Thr Cys Thr Phe Lys Glu Leu Val Tyr Glu Thr Val 450                                         480
AGA GTG CCC GGC TGT GCT CAC CAT GCA GAT TCC TTG TAT ACA TAC CCA GTG GCC ACC CAG
Arg Val Pro Gly Cys Ala His His Ala Asp Ser Leu Tyr Thr Tyr Pro Val Ala Thr Gln 510                                         540
TGT CAC TGT GGC AAG TGT GAC AGC GAC AGC ACT GAT TGT ACT GTG CGA GGC CTG GGG CCC
Cys His Cys Gly Lys Cys Asp Ser Asp Ser Thr Asp Cys Thr Val Arg Gly Leu Gly Pro

570
AGC TAC TGC TCC TTT GGT GAA ATG AAA GAA  TAA   AAA TCA GTG GAC ATT TC
Ser Tyr Cys Ser Phe Gly Glu Met Lys Glu  End
```

Still referring to the above sequence, there is a box around the ATG initiation codon of the 18 amino acid signal peptide, which is cleaved post-translationally. The mature protein begins with the amino acid Asn encoded by the circled triplet AAT. The exon-intron boundaries are marked by arrows; they are flanked by the concesus sequence GT for the splice donor and AG for the splice acceptor site. There is a box around the stop codon TAA, the end of the coding region.

Below is a reproduction of the above sequence not broken into triplets, showing restriction sites; the ATG beginning and the TAA ending the coding region are boxed and the exon-intron junctions are marked by arrows.

```
           10         20         30         40         50         60
     GCTTACATAA TGATTATCGT TCTTTGGTTT CTCAGTTTCT AGTGGGCTTC ATTGTTTGCT
                                D
                                D
                                E
                                1

70         80         90        100        110        120
     TCCCAGACCA GG  ATG   AAGAC ACTCCAGTTT TTCTTCCTTT TCTGTTGCTG GAAAGCAATC
              B  F    N                        N
              S  O    B                        B
              T  K    O                        O
              1  1    2                        2

130        140        150        160        170        180
     TGCTGCAATA GCTGTGAGCT GACCAACATC ACCATTGCAA TAGAGAAAGA AGAATGTCGT
              B        A          A          N                  N
              B        L          L          P                  B
              V        U          U          N                  D
              1        1          1          1                  2

190        200        210        220        230  ↓    240
     TTCTGCATAA GCATCAACAC CACTTGGTGT GCTGGCTACT GCTACACCAG GGTAGGTACC
              S                                         R       KR
              F                                         S       PS
              A                                         T       NA
              1                                         1       1 1
```

```
              250        260        270        280        290        300
// ATGTTAG AGCAAGCAGT ATTCAATTTC TGTCTCATTT TGACTAAGCT AAATAGGAAC
                                             D  A
                                             D  L
                                             E  U
                                             1  1

310        320        330        340   ↓    350        360
   TTCCACAATA CCATAACCTA ACTCTCTTCT TAAACTCCTC AGGATCTGGT GTATAAGGAC
                           N          SD       XS              A
                           S          AD       NA              V
                           O          UE       OU              A
                           2          1 1      2 A             2

370        380        390        400        410        420
   CCAGCCAGGC CCAAAATCCA GAAAACATGT ACCTTCAAGG AACTGGTATA TGAAACAGTG
        B  S              A    R
        S  A              F    S
        T  U              L    A
        1  1              3    1

430        440        450        460        470        480
   AGAGTGCCCG GCTGTGCTCA CCATGCAGAT TCCTTGTATA CATACCCAGT GGCCACCCAG
        HN     H    N     N         S              B H
        CP     G    P     I         N              A A
        I A    I    N     N         A              L E
        1 2    1    1     1         1              1 3

490        500        510        520        530        540
   TGTCACTGTG GCAAGTGTGA CAGCGACAGC ACTGATTGTA CTGTGCGAGG CCTGGGGCCC
                                    R            MS N  B     A S
                                    S            NTA   S     P A
                                    A            LUE   T     A U
                                    1            1 1 3 1     1 1

550        560        570        580        590
   AGCTACTGCT CCTTTGGTGA AATGAAAGAA  TAA  AGATCAG TGGACATTTC
   A           N                     S
   L           P                     A
   U           N                     U
   1           1                     1
```

Insertion of the Beta FSH DNA into a BPV-Based Expression Vector

Figure 4:
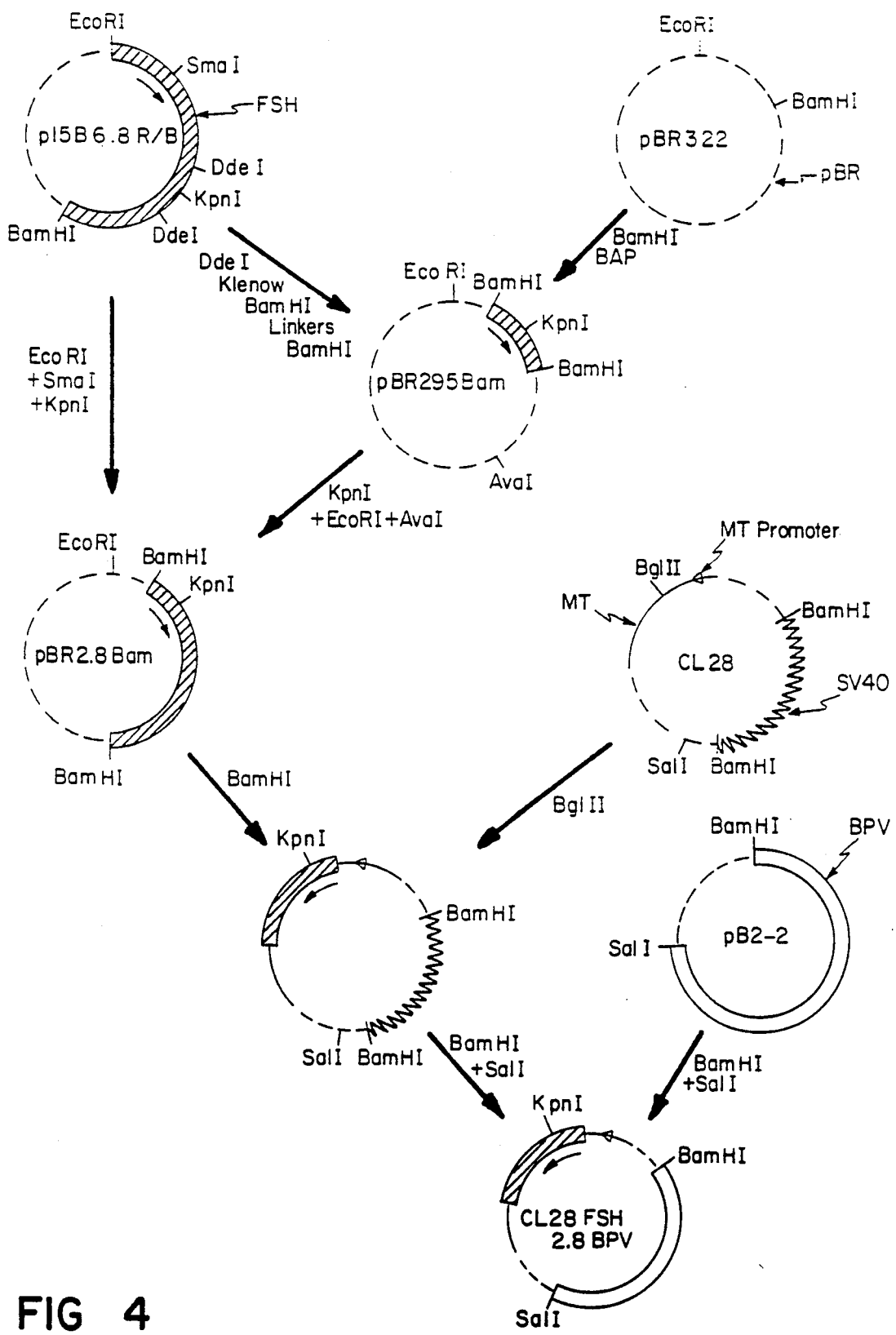
FIG. 4 is a diagrammatic illustration of the construction of the BPV-containing plasmid CL28FSH2.8BPV, encoding the beta subunit of FSH.

Referring to FIG. 3, a synthetic BamHI linker is inserted at the DdeI site of p15B6.8R/B, which is located 42 nucleotides 5' of the ATG initiation codon. Referring to FIG. 4, p15B6.8R/B is digested with DdeI and treated with E. coli DNA polymerase (Klenow), after which it is ligated to synthetic BamHI linkers and digested with BamHI. The 295 bp fragment containing the first exon of FSH is isolated and cloned into the BamHI site of pBR322. The resulting plasmid pBR295Bam is digested with KpnI plus EcoRI plus AvaI and ligated to p15B6.8R/B which has been digested with KpnI plus EcoRI plus SmaI. The ligation mix is then used to transform E. coli, and the plasmid pBR2.8Bam containing the human beta FSH DNA sequence as a BamHI fragment is identified from among the transformants by restriction mapping.

As shown in FIG. 4, expression plasmid CL28FSH2.8BPV is prepared according to the same method used to prepare pRF375 (FIG. 1), except that the 2.8 kb BamHI fragment of pBR2.8Bam is used in place of the alpha hCG cDNA clone. Plasmid CL28FSH2 8BPV can be used to transform mammalian host cells using conventional methods, and human beta FSH can be isolated and purified.

Transfection of Mouse Cells

To produce heterodimeric FSH using a mixed transfection, five μg of each BPV plasmid, i.e., pRF375 (alpha subunit) and CL28FSH2.8BPV (beta FSH), are mixed and added 0.5 ml of a 250 mM CaCl, solution containing 10 μg of salmon sperm DNA as carrier. This mixture is bubbled into 0.5 ml 280 mM NaCl, 50 mM Hepes and 1.5 mM sodium phosphate. The calcium phosphate precipitate is allowed to form for 30–40 minutes at room temperature.

24 hours prior to transfection, $5 \times 10^5$ cells of mouse C127 cells (available from Dr. Dean Hamer, National Cancer Institute, NIH, Bethesda, MD) are placed in a 100 mm dish or T-75 flask. Immediately before adding the exogenous DNA, the cells are fed with fresh medium (Dulbecco's Modified Medium. 10% fetal calf serum). One ml of calcium phosphate precipitate is added to each dish (10 ml), and the cells are incubated for 6–8 hours at 37° C.

The medium is aspirated and replaced with 5 ml of 2 glycerol in phosphate buffered saline, pH 7.0 (PBS) for 2 minutes at room temperature. The cells are washed with PBS, fed with 10ml of medium, and incubated at 37° C. After 20–24 hours, the medium is changed and subsequent refeeding of the cells is carried out every 3–4 days. Individual clones are grown in T-25 flasks. After 7–21 days, cell clones can be transferred to larger flasks for analysis.

Deposits

The following, described above, has been deposited in the Agricultural Research Culture Collection (NRRL), Peoria, IL 61604:

CL28FSH2.8BPV in *E. coli*, NRRL B-15923

The following, described above, has been in the American Type Culture Collection, Rockville, MD:
pRF375 in C127 cells, ATCC CRL 8401.

Applicants' assignee, Integrated Genetics, Inc., acknowledges its responsibility to replace these cultures should they die before the end of the term of a patent issued hereon, and its responsibility to notify the ATCC and NRRL of the issuance of such a patent, at which time the deposits will be made available to the public. Until that time the deposits will be made available to the Commissioner of Patents under the terms of 37 CFR §1.14 and 35 USC §112.

USE

The transformed cell lines of the invention are used to produce glycosylated, biologically active heterodimeric human FSH, which is purified from the cells and/or their culture media using conventional purification techniques. FSH has a number of well-known medical uses associated with human fertility. For example, FSH can be used, alone or in conjunction with hCG or LH, to induce ovulation, or superovulation for in vitro fertilization.

In addition, heterodimeric FSH, or the beta subunit alone, can be used in diagnostic tests for fertility and pituitary functions.

FSH produced by recombinant cells has the advantage, compared to FSH obtained from natural sources, of being free from contamination by other human proteins, in particular other fertility hormones.

Other embodiments are within the following claims. For example, rather than producing heterodimeric FSH by culturing cells containing two separate expression vectors, one encoding the alpha subunit and the other encoding the beta subunit, DNA encoding both subunits can be included in the same expression vector.

We claim:

1. A mammalian cell comprising a transformed cell transformed by at least a first expression vector, said transformed cell being capable of producing a biologically active heterodimeric human fertility hormone comprised of an alpha subunit and a beta subunit, each said subunit being encoded in nature by a distinct mRNA, said hormone being human FSH, the alpha subunit of said hormone being encoded by said first expression vector and the beta subunit of said hormone being encoded by said first expression vector or by a second expression vector by which said transformed cell is also transformed, or progeny of said transformed cell containing the genetic information imparted by said vector or vectors.

2. A mammalian cell in accordance with claim 1, said first vector being a plasmid.

3. A mammalian cell in accordance with claim 1, the alpha and beta subunits of said heterodimeric hormone being encoded by said first expression vector.

4. A mammalian cell in accordance with claim 1, transcription of the alpha and beta subunits of said heterodimeric hormone being under the control of the mouse metallothionein promoter.

5. A mammalian cell in accordance with claim 1, said cell being a mouse cell.

6. A mammalian cell in accordance with claim 1, said first expression vector being autonomously replicating.

7. A mammalian cell in accordance with claim 1, wherein said beta subunit is encoded by a second expression vector, distinct from said first expression vector, said transformed cell also being transformed by said second expression vector.

8. A mammalian cell in accordance with claim 7, said second expression vector being autonomously replicating.

9. A method for producing the biologically active human fertility hormone FSH comprising culturing host mammalian cells in accordance with claim 1.

10. The method of claim 9, wherein said beta subunit is encoded by a second expression vector, distinct from said first expression vector, said transformed cell also being transformed by said second expression vector, and wherein each said expression vector is autonomously replicating.

* * * * *